United States Patent [19]

de Haar et al.

[11] Patent Number: 5,026,430

[45] Date of Patent: Jun. 25, 1991

[54] METHOD OF PREPARING LACTULOSE

[75] Inventors: Walterus T. de Haar; Hendrik Pluim, both of Weesp, Netherlands

[73] Assignee: Duphar International Research B.V., Weesp, Netherlands

[21] Appl. No.: 566,314

[22] Filed: Aug. 13, 1990

Related U.S. Application Data

[63] Continuation of Ser. No. 342,882, Apr. 25, 1989, abandoned.

[30] Foreign Application Priority Data

Apr. 28, 1988 [NL] Netherlands ......................... 8801102

[51] Int. Cl.$^5$ ............................................. C08B 30/00
[52] U.S. Cl. ..................................................... 127/34
[58] Field of Search ........................... 127/46.2, 46.3; 536/124, 125

[56] References Cited

U.S. PATENT DOCUMENTS 3,707,534 12/1972 Nitsch et al. ......................... 536/125
4,196,017 4/1980 Melville et al. ......................... 127/41
4,536,221 8/1985 Carrobbi et al. ................... 127/46.2

Primary Examiner—Theodore Morris
Assistant Examiner—P. L. Hailey
Attorney, Agent, or Firm—Stevens, Davis, Miller & Mosher

[57] ABSTRACT

The invention relates to a new method of preparing lactulose by basic isomerization of lactose. According to the invention the reaction mixture is treated with hydrogen peroxide or sodium chlorite to obtain lactulose of an acceptable color for a pharmaceutical product.

Preferably 0.5–5 g of hydrogen peroxide are used per kg of lactose.1H$_2$O.

5 Claims, No Drawings

METHOD OF PREPARING LACTULOSE

This application is a continuation of application Ser. No. 342,882, filed Apr. 25, 1989, now abandoned.

The invention relates to a new method of preparing lactulose by basic isomerisation of lactose.

A conventional method of preparing lactulose from lactose comprises the basic isomerisation of lactose at elevated temperature. During the said isomerisation reaction are formed—in addition to lactulose—decomposition products thereof, and a brown-coloured reaction mixture is obtained.

It is known that the brown colouring of the mixture during the isomerisation can be mitigated by carrying out the isomerisation in the presence of sodium sulphite, sodium bisulphite or sodium phosphite. It is assumed that the sulphite ion, bisulphite ion or phosphite ion reacts with the decomposition products of lactulose while forming sugar sulphonic acids and sugar phosphonic acids which can then be removed by means of ion exchangers.

Such a method is known from Netherlands patent specification No. 165467 in which the use of sodium sulphite, from U.S. Pat. No. 4,536,221 in which the use of sodium bisulphite, and from Netherlands patent application No. 7907259 in which the use of sodium phosphite as an oxidant is described. However, the formed sugar sulphonic acids and sugar phosphonic acids are hard to decompose on purifying the waste water in a water treatment plant and hence they are ecologically unsound.

It has now been found that such problems do not present themselves when hydrogen peroxide or sodium chlorite is used in the method mentioned in the preamble instead of sulphite, bisulphite or phosphite.

Hydrogen peroxide both in an acid medium and in a basic medium may serve as an oxidant and consequently can oxidize the decomposition products of lactulose which are formed during the isomerisation to (carboxylic) acids which can be removed by means of ion exchangers.

Excellent results are also obtained with sodium chlorite as a coreagent besides the sodium hydroxide required for the isomerisation, but as a result of the formation of corrosive compounds, for example, chlorine and chlorodioxide, during the reaction, higher requirements are imposed on the apparatus than when hydrogen peroxide is used.

According to a preferred embodiment of the method according to the invention hydrogen peroxide is used as an oxidant and is added after the basic isomerisation reaction of lactose to lactulose.

It is recommendable in particular to add hydrogen peroxide, for example, in the form of 17.5% solution, to the isomerisation mixture at a temperature of approximately 50° C., after the pH of the mixture has become smaller than 7. However, it is also possible to add hydrogen peroxide at a higher temperature of approximately 95° C. under basic conditions (pH 7.5–8.0).

The reaction mixture, after isomerisation and treatment with $H_2O_2$ or $NaClO_2$, is processed in the conventional manner. The non-converted lactose is removed by crystallisation and is used again. The mixture comprising lactulose and decomposition products is purified by means of ion exchangers.

By using $H_2O_2$ or $NaClO_2$ instead of $Na_2SO_3$, $NaHSO_3$ and $Na_3PO_3$ used so far, the decomposition products of lactulose which are formed during the isomerisation are converted into readily decomposable sugar carboxylic acids which cause no problems ecologically.

EXAMPLE I

The data and results of a number of experiments on a laboratory scale are recorded in table A hereinafter. In all the experiments the isomerisation of lactose to lactulose was carried out with NaOH, optionally in the presence of $Na_2SO_3$. The addition of $H_2O_2$ according to the invention after the isomerisation reaction was carried out in two different manners:

method I: in basic conditions (pH 7.5–8) at approx. 95° C.

method II: in acid conditions (pH <7) at approx. 50° C.

TABLE A

| Exp. No. | NaOH g/kg lactose.1H$_2$O | Na$_2$SO$_3$ (ditto) | H$_2$O$_2$ (ditto) | Method | Colour after isomerisation* |
|---|---|---|---|---|---|
| 1 | 2.5 | — | — | — | 13–16 |
| 2 | 2.0 | 2.0 | — | — | 3–10 |
| 3 | 2.5 | — | 2.4 | I | 2–3 |
| 4 | 2.5 | — | 2.4 | II | 6–7 |

*The colour is compared with the Gardner scale, a colour scale from 1 (colourless) to 20 (reddish brown).

On the basis of the colourindex the use of $H_2O_2$ according to method I were to be preferred. On the basis of results of stability experiments (ageing tests), however, it seems that method II leads to a slightly better result.

EXAMPLE II

The data and results of a number of experiments on a laboratory scale are recorded in table B. As in example I in all the experiments the isomerisation was carried out with NaOH, optionally in the presence of $Na_2SO_3$. The addition of $NaClO_2$ was carried out simultaneously with the addition of NaOH at about 95° C.

TABLE B

| Exp. No. | NaOH g/kg lactose.1H$_2$O | Na$_2$SO$_3$ (ditto) | NaClO$_2$ (ditto) | Colour after isomerisation* |
|---|---|---|---|---|
| 5 | 2.5 | — | — | 13–16 |
| 6 | 2.0 | 2.0 | — | 3–10 |
| 7 | 1.9 | — | 2.7 | 3–8 |
| 8 | 3.5 | — | 1.2 | 13–16 |
| 9 | 3.5 | — | 3.9 | 3–8 |

*Gardner scale

We claim:

1. A method of preparing lactulose by basic isomerization of lactose, comprising basically isomerizing lactose with sodium hydroxide to produce a reaction mixture; and
   treating the reaction mixture with hydrogen peroxide or sodium chlorite in an amount effective to produce oxidation of decomposition products which can be removed by means of ion exchangers.

2. A method as claimed in claim 1, characterised in that 0.5–5 g of $H_2O_2$ are used per kg of lactose. 1H$_2$O.

3. A method as claimed in claim 2 or 1, characterised in that $H_2O_2$ is added at a pH of 5.0–7.0, and at 40°–80° C.

4. A method as claim in claim 2 or 1, characterised in that $H_2O_2$ is added in basic conditions at a pH of 7.5–8.0 and at 90°–100° C.

5. A method as claimed in claim 1, characterized in that 1–5 g of $NaClO_2$ are used per kg of lactose. 1H$_2$O at a temperature of 90°–100° C.

* * * * *